US011197761B2

(12) United States Patent
Cornelis

(10) Patent No.: US 11,197,761 B2
(45) Date of Patent: Dec. 14, 2021

(54) SYSTEM FOR DIRECTED INTRAOSSEOUS INJECTION OF SURGICAL CEMENT

(71) Applicant: CENTRE HOSPITALIER UNIVERSITAIRE DE BORDEAUX, Talence (FR)

(72) Inventor: François Cornelis, Talence (FR)

(73) Assignee: CENTRE HOSPITALIER UNIVERSITAIRE DE BORDEAUX, Talence (FR)

( * ) Notice: Subject to any disclaimer, the term of this patent is extended or adjusted under 35 U.S.C. 154(b) by 0 days.

(21) Appl. No.: 16/098,922

(22) PCT Filed: May 4, 2017

(86) PCT No.: PCT/FR2017/051077
§ 371 (c)(1),
(2) Date: Nov. 5, 2018

(87) PCT Pub. No.: WO2017/191419
PCT Pub. Date: Nov. 9, 2017

(65) Prior Publication Data
US 2019/0083267 A1    Mar. 21, 2019

(30) Foreign Application Priority Data

May 6, 2016   (FR) ...................................... 1654105

(51) Int. Cl.
*A61F 2/28*    (2006.01)
*A61B 17/70*   (2006.01)
(Continued)

(52) U.S. Cl.
CPC ........ *A61F 2/2846* (2013.01); *A61B 17/7097* (2013.01); *A61B 17/7098* (2013.01);
(Continued)

(58) Field of Classification Search
CPC ........ A61F 2/2846; A61F 2/4601; A61F 2/44; A61F 2/88; A61F 2002/9583;
(Continued)

(56) References Cited

U.S. PATENT DOCUMENTS 9,126,023 B1 *   9/2015   Sahatjian ............... A61M 25/10
9,247,970 B2 *   2/2016   Teisen ................. A61B 17/8872
(Continued)

OTHER PUBLICATIONS

"Cannula." Merriam-Webster.com Dictionary, Merriam-Webster, https://www.merriam-webster.com/dictionary/cannula. Accessed Feb. 24, 2021 (Year: NA).*
Written Opinion in International Application No. PCT/FR2017/051077, dated Aug. 10, 2017, pp. 1-7.

*Primary Examiner* — Kevin T Truong
*Assistant Examiner* — Lisa Nguyen
(74) *Attorney, Agent, or Firm* — Saliwanchik, Lloyd & Eisenschenk

(57) ABSTRACT

The invention relates to a system (10) for the intraosseous injection of surgical cement comprising an external sleeve (11); a cannula (13) mounted coaxially in the external sleeve, said cannula being able to be moved along a longitudinal axis (A) in the external sleeve, the cannula being provided with a tapered distal point (15); and a stent (18) accommodated in the interior of the external sleeve, said stent being mounted around a distal end (16) of the cannula. The invention also relates to a kit comprising a system of this type for the injection of surgical cement, surgical cement injection means capable of being connected to the proximal end of the internal cannula, and possibly surgical cement.

15 Claims, 3 Drawing Sheets

Figure 1:
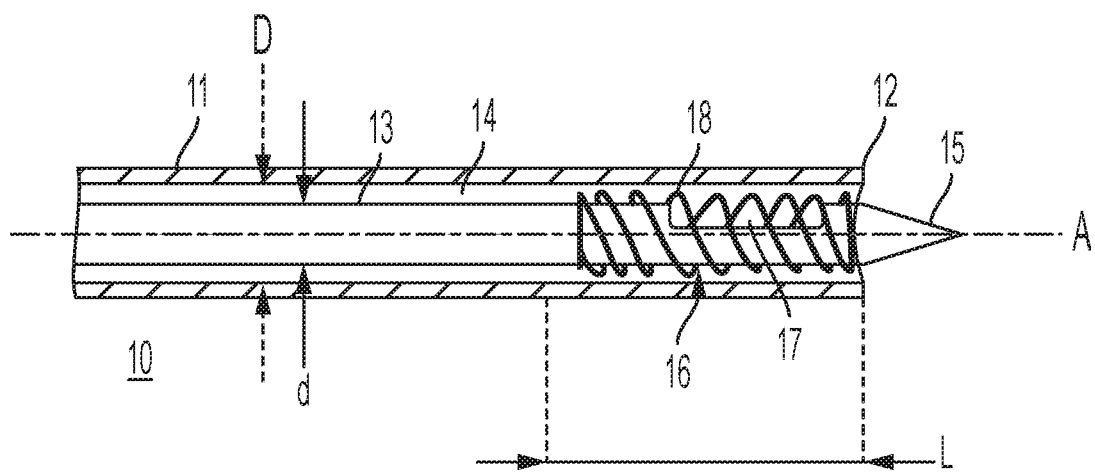

(51) Int. Cl.
*A61F 2/44* (2006.01)
*A61F 2/46* (2006.01)
*A61B 17/88* (2006.01)
*A61F 2/88* (2006.01)

(52) U.S. Cl.
CPC ............ *A61B 17/8858* (2013.01); *A61F 2/44* (2013.01); *A61F 2/4601* (2013.01); *A61F 2/88* (2013.01); *A61F 2210/0014* (2013.01)

(58) Field of Classification Search
CPC . A61F 2/962; A61F 2/94; A61F 2/966; A61B 17/7097; A61B 17/7098; A61B 17/8802; A61B 17/8005; A61B 17/1811; A61B 2017/8813; A61B 17/8816
See application file for complete search history.

(56) References Cited

U.S. PATENT DOCUMENTS

| | | | | |
|---|---|---|---|---|
| 10,085,783 | B2* | 10/2018 | Emery | A61B 17/8811 |
| 2006/0100706 | A1* | 5/2006 | Shadduck | A61B 17/1617 |
| | | | | 623/17.11 |
| 2007/0088436 | A1 | 4/2007 | Parsons et al. | |
| 2011/0046737 | A1 | 2/2011 | Teisen | |
| 2015/0282852 | A1* | 10/2015 | Truckai | A61B 17/8827 |
| | | | | 606/279 |
| 2015/0335370 | A1* | 11/2015 | Sahatjian | A61B 17/8811 |
| | | | | 606/94 |
| 2016/0095640 | A1* | 4/2016 | Sennett | A61B 17/8858 |
| | | | | 606/94 |

* cited by examiner

SYSTEM FOR DIRECTED INTRAOSSEOUS INJECTION OF SURGICAL CEMENT

CROSS-REFERENCE TO RELATED APPLICATION

This application is the U.S. national stage application of International Patent Application No. PCT/FR2017/051077, filed May 4, 2017.

The invention has as its object a system allowing the intraosseous injection of surgical cement, particularly at low pressure. The system according to the invention is particularly suited to the consolidation of a weakened bone, particularly of a vertebral body, or of a pathological (malignant or benign) lytic osseous lesion regardless of its location.

For several decades, percutaneous injection of cement, such as cementoplasty, has been developed so as to repair osseous trauma (vertebral collapse) or to fill in lytic osseous lesions (osteolytic metastases). This injection of cement, particularly polymeric cement, must allow bone filling with mechanical properties substantially equivalent to those of the damaged bone. Advantageously, this bone consolidation is generally accompanied by a rapid reduction in bone pain in the patient.

At first, the systems developed allowed the direct injection of cement into the zone to be treated (with radiological monitoring). Thus, cement injection is practiced by percutaneous injection of cement through a needle, or trocar, introduced directly into the vertebral body or into the affected bone. Cement injection is in particular used in the treatment of osteoporotic fractures, or in certain tumors, for reinforcing affected vertebrae. However, the risks of cement leaking toward the exterior of the osseous body are high due to the absence of constraint during injection. Now, due to vascularization, cement can quickly find itself in the venous system of the patient, with high risks of migration to the epidural and/or pre-vertebral veins, which can cause pulmonary embolisms.

Alternative systems have also been developed.

Thus cyphoplasty, or kyphoplasty, is very widely used in patients having, in addition to a vertebral fracture, a collapse of the vertebra. This technique is particularly suited in the context of the treatment of bone fractures with vertebral crushing, particularly with young adults after trauma, because it allows the patient to recover a greater vertebral height. Kyphoplasty consists of introducing a cuff percutaneously, through a trocar, into the fractured vertebral body. Once set in place, the cuff is inflated so as to recover the vertebral height progressively. The pressure that is used is then high. The cuff is then withdrawn and cement is injected in its place, without resistance. However, after the deflation and withdrawal of the cuff, and prior to the injection of cement, a partial loss of height, and therefore insufficient correction causing a persistence of spinal pain, is frequently observed.

In the last few years, systems for reducing vertebral fractures using vertebral stents have been implemented. The stent is usually introduced simultaneously with the cuff and maintains the opening of the vertebral body between the step of withdrawing the cuff and the injection of cement. The pressure applied remains high. This technology, known in particular by the name "stentoplasty" or VBS for "vertebral body stenting", further has the advantage of containing the majority of the cement in the volume of the stent, thus limiting the risks of leakage.

Current systems used for performing a stentoplasty are, however, complex in design and in use. They require multiple and successive manipulations of trocars, cuff inflation then withdrawal means, means of injecting cement, etc., making the intervention difficult. Furthermore, these systems are particularly dedicated to traumatic vertebral fractures and cannot be easily transposed to the treatment of other osseous lesions, caused in particular by metastatic bone cancer. The pressure used is prohibitive, the risk of associated tumor migration being too high. In addition, the osteolytic character of the lesions does not allow the deployment of this equipment in a healthy zone.

At this time, therefore, there does not exist a satisfactory device allowing the intraosseous injection of cement at low pressure in a simple and reliable manner, regardless of the position and the nature of the bone to be treated.

It is the purpose of the invention to resolve at least partially the problem mentioned above, by proposing a single device allowing not only the installation of a stent in an osseous body, but also the injection, advantageously directed, after the installation of said stent in the osseous body, of bone cement in the volume of said stent. The system according to the invention does not require the use of an extrinsic expansion mechanisms of the stent, and advantageously allows the installation of a stent/cement assembly having synergetic biomechanical properties. The device according to the invention comprises in particular means of inserting a stent, capable of bringing the stent to the fracture or osseous lesion to be treated and to allow its deployment once in position. More precisely, a system of concentric tubes which can be movable with respect to one another allows, successively, the stent to be held in a constrained state, bringing it to the zone to be treated, then freeing it so that it deploys simultaneously with or prior to injecting cement into the internal volume of said stent. Thus, the means of installation of the stent according to the invention are also used for the injection of cement, which allows limiting the number of manipulations and simplifies the surgical procedure as a whole, allowing a rapid and simple implementation. To facilitate the penetration into the osseous body, the system further has a sharp end facilitating perforation and progression into the bone.

The invention therefore has as its object a system for the intraosseous injection of surgical cement comprising:
    an external sleeve;
    an internal cannula mounted coaxially in the external sleeve, said cannula being able to be moved along a longitudinal axis in the external sleeve, the cannula being provided with a tapered distal point; and
    a stent accommodated in the interior of the external sleeve, said stent being mounted around a distal portion of the cannula.

In the context of the invention, "distal" designates a portion of an element which is farthest away from the preemption zone of said element, in opposition to the "proximal" portion. Generally, the distal portion of an element of the system designates a portion of said element designed to penetrate the body of a patient, by opposition to the proximal portion.

According to the invention, the external sleeve and the cannula advantageously have a generally hollow cylindrical, or tubular shape. The sleeve and the cannula are coaxial, or concentric. The outer diameter of the cannula is strictly less than the internal diameter of the sleeve, so that said cannula, mounted in said sleeve, can move axially in the sleeve.

According to the invention, the distal end of the cannula includes a tapered point, designed to facilitate the insertion of the system into the osseous body. Advantageously, said point leads to the distal end of the external sleeve. The point thus forms the distal end of the system, which comes first into contact with the body of the patient in which the stent must be accommodated, so as to be able to pierce the different portions of said body, until the target osseous body. The distal point of the cannula can thus protrude from the distal end of the sleeve, or simply lie flush with the orifice of the distal end of the sleeve.

In one particular embodiment, the distal end of the sleeve includes a beveled point, designed to facilitate the insertion of the system into the body of the patient. In another embodiment, the distal end of the sleeve has a straight cross section.

In one embodiment, the proximal end of the cannula, opposite to the distal end, is provided with coupling means capable of being connected to surgical cement injection means. The coupling means can for example consist of a thread provided on the proximal end of the cannula, said thread, external or internal, then being complementary to a thread provided on the means of injection. The coupling means can also consist of interlocking means, clips, etc.

In one particular embodiment, the coupling means allow sealed coupling with the cement injection means.

In one particular embodiment, the cannula comprises a lateral opening, capable of allowing surgical cement to leave the cannula when it is injected into the internal volume of said cannula. Advantageously, the lateral opening is provided in a distal portion of said cannula, designed to be inserted into the osseous body to be treated, so that the cement can be released into said osseous body.

According to the invention, in a configuration prior to use, the stent is mounted in a constrained state in the internal volume of the distal portion of the sleeve. A distal portion of the cannula is in contact with the stent, so that the departure of the distal portion of the cannula from the sleeve also forces the stent out of said sleeve. For example, the stent is mounted around the external wall of the distal portion of the cannula. Thus, the stent is held in the internal volume of the sleeve, between the internal wall of said sleeve and the external wall of the cannula.

Advantageously, the stent is a self-expanding stent. In one particular embodiment, the stent is wound around the distal portion of the cannula, so as to be constrained between the external wall of the cannula and the internal wall of the sleeve. By moving the cannula in a distal direction with respect to the sleeve, and/or by moving the sleeve in a proximal direction with respect to the cannula, the stent is released, and no longer being constrained by the wall of the sleeve, it is deployed in the osseous body around the distal portion of the cannula. It is then possible to withdraw the cannula from the osseous body without moving the stent.

In one embodiment of the invention, the system is provided with reversible blocking means, capable of preventing any involuntary movement of the cannula with respect to the sleeve, or conversely. The blocking means make it possible to ensure holding in position of the tapered point of the cannula with respect to the sleeve during the insertion of the system until the target osseous body. The blocking means can then be un-blocked to allow the movement of the sleeve and/or of the cannula with respect to one another. The blocking means can for example consist of complementary threads on the cannula and the sleeve. For example, an internal wall of the proximal portion of the sleeve comprises a thread complementary with a thread provided on the external wall of the proximal portion of the cannula. It is them impossible to modify accidentally the position of the cannula in the sleeve. A rotation of one with respect to the other is necessary to allow any movement.

In another example, the blocking means can consist of one or more retractable lugs on the external wall of the cannula and accommodated, in a first configuration, in one or more complementary openings in the wall of the sleeve. To allow the movement of the cannula in the sleeve, it is then necessary to retract the lug(s), for example by exerting pressure on them.

According to the invention, the system for injecting cement can be provided with monitoring means allowing the assurance of the total release of the stent. For example, a marking is provided on the cannula, indicating to the user the maximum and/or minimum movement distance of the sleeve in a proximal direction, and/or of the cannula in a distal direction, to guarantee the release of the stent. In one particular embodiment, the blocking means also serve as monitoring means for guaranteeing a sufficient axial movement of the cannula in the sleeve and/or to limit this movement. For example, the screw pitch of the threads on the cannula and the sleeve is calculated to allow a movement of one with respect to the other over a sufficient distance to guarantee the total release of the stent from the internal volume of the sleeve. In the case of retractable lugs, it is possible to provide a second series of openings on the sleeve, upstream from the first series. The movement of the cannula in the sleeve is thus limited to the distance between the two series of openings. In the context of the invention, the terms "upstream" and "downstream" are understood to mean with respect to the direction of penetration of the system in a target osseous body, upstream designating the portion closest to said target osseous body. Of course, a simple visual marking, for example at the proximal portions of the cannula and/or of the sleeve can be used as monitoring means.

Advantageously, the stent is a self-expanding stent made of shape-memory material, so that once released out of the external sleeve, the stent deploys to retrieve at least partially the desired initial shape. The injection of the cement can also participate in the complete deployment of the stent in the osseous body. For example, the shape-memory stent is made of nickel/titanium (Nitinol), cobalt-chromium or platinum-chromium alloy. In another embodiment, the stent is made of polymers, such as poly-lactic acid (PLA).

In one particular embodiment, the stent is covered with an external shell designed to prevent or limit cement leakage. Advantageously, an external envelope of this type is made of stretchable or elastic material, at least partially waterproof. Advantageously, the external envelope conforms to an external contour of the stent. In one particular embodiment, the external shell is made of polytetrafluoroethylene (PTFE).

The general shape of the system according to the invention can advantageously adapt to the morphology of the osseous body to be treated. Thus, in one embodiment, the distal portion of the system, and more particularly the distal portion of the external sleeve and of the cannula, has a straight profile. By profile is meant the external contour of the element considered. In another embodiment, the distal portion of the external sleeve and of the cannula has a curved profile, the curve of the sleeve and of the cannula being identical. This last configuration is particularly adapted to the treatment of the bones of the hip or of the ribs.

In one particular embodiment, the external sleeve has an external diameter comprised between 0.2 and 0.5 cm (or between 7 and 15 gauge), preferably between 0.3 and 0.4 cm, and a length comprised between 10 and 15 cm. The cannula can then have a diameter comprised between 0.1 and 0.4 cm (or between approximately 6 and 18 gauge), and preferably between 0.2 and 0.35 cm. Generally, the dimensions of the external sleeve and of the cannula are adapted to the body of the patient to be treated, the position of the target osseous body in said body and the nature of the osseous lesion to be treated.

The stent can have variable dimensions (and particularly length and diameter) depending on the nature and the size of osseous lesion to be treated. The stent generally does not fill the entire lesion, but must at least allow the formation of a pillar in said lesion to distribute the loads between the regions of the osseous body around the lesion. For example, the stent has a diameter comprised between 0.8 and 1.6 cm, for a length (or large dimension) comprised between 4 and 6 cm.

The invention also has as its object an intraosseous surgical cement injection kit comprising, besides the cement injection system described above, cement injection means capable of being connected to the proximal end of the cannula, and possibly surgical cement. For example, the means of injection consist of a syringe of which the injection end is coupled to the proximal end of the cannula. The injection end, possibly equipped with a needle, could thus be inserted into the proximal portion of the cannula. The insertion of the piston into the body of the syringe, previously filled with surgical cement, allows the cement to be injected into the cannula.

According to the invention, any surgical cement suited to intraosseous use can be used. Cements of the PMMA (poly methyl methacrylate) type commonly used in vertebroplasty can be mentioned as a non-limiting example.

The kit can include already assembled elements of the injection system, i.e. the cannula and the stent accommodated in the external sleeve, or rather said elements ready for assembly.

In one embodiment, the injection means comprise thrusting means designed to make the cement penetrate into the interior of the cannula and force it up to the stent. For example, the injection means comprise a piston designed to be inserted into the cannula, from the proximal end, and capable of sliding axially in said cannula in the direction of the distal end.

The system according to the invention, in which the stent is mounted around the distal portion of the cannula, can be used in a method for injecting surgical cement into a target osseous body of a patient comprising the steps consisting of:

Introducing the distal end of the cannula into the body of the patient;
Continuing the insertion of the cannula and of the external sleeve up to the target osseous body;
Sliding at least partially the external sleeve out of the osseous body so as to free the stent;
Beginning the injection of surgical cement into the internal volume of the stent by means of the cannula;
Progressively sliding the cannula out of the stent and of the osseous body while still continuing the injection of the surgical cement, so as to gradually fill the internal volume of the stent from the distal end to the proximal end of said stent;
Withdrawing the external sleeve and the cannula from the body of the patient.

It is possible of course to begin the injection of cement simultaneously with the withdrawal of the cannula. Generally, once the stent is ejected from the external sleeve, the cannula can be used to inject cement into the internal volume of said stent.

Figure 2:
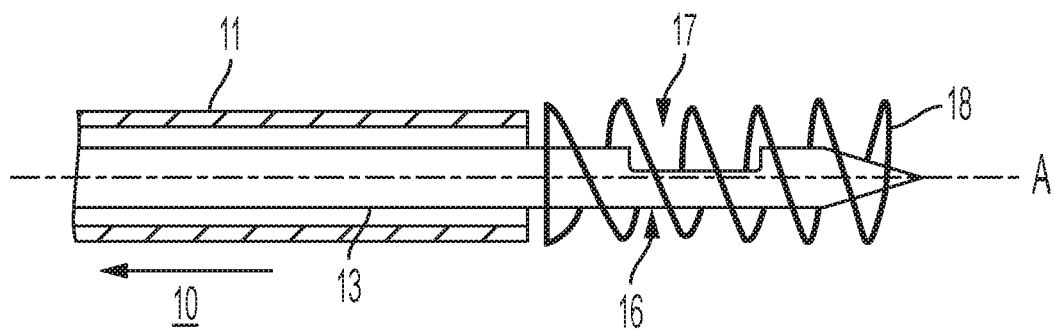
Figure 3:
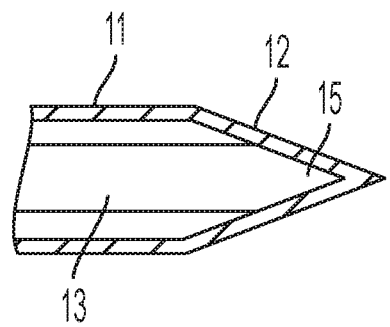
Figure 4A:
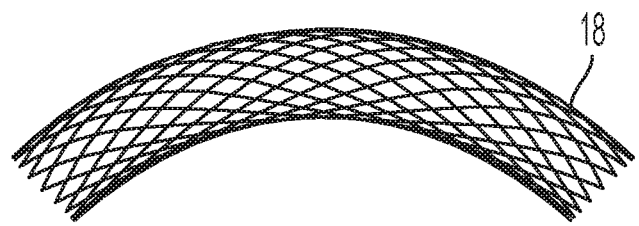
Figure 4B:
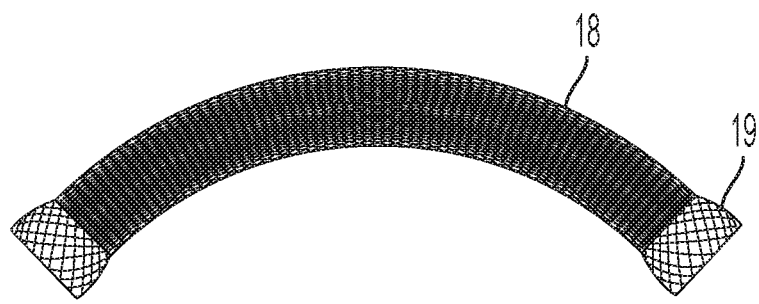

The invention also has as its object a treatment method for an osseous body, such as a vertebra, comprising the steps above. The invention will be better understood upon reading the description which follows and upon examination of the figures that accompany it. These are presented by way of indication and in no way limit the invention. The figures show:

FIG. 1: a partial schematic view in longitudinal section of the system for intraosseous injection of surgical cement according to an embodiment of the invention, prior to use;

FIG. 2: a schematic view of the system for intraosseous injection of surgical cement of FIG. 1, in use;

FIG. 3: a schematic view in longitudinal section of the distal end of the system for intraosseous injection of surgical cement according to one embodiment of the invention;

FIGS. 4A and 4B: two examples of stents which can be used in the system for injecting osseous cement according to the invention;

FIGS. 5A-5G: schematic views of the system for intraosseous injection of surgical cement according to an embodiment of the invention, during the different steps of a stentoplasty method.

A partial view is shown in FIG. 1 of a system for injecting cement 10 according to one embodiment of the invention. More precisely, the system 10 includes an external sleeve 11 with a generally cylindrical shape with a straight circular cross-section. A distal end 12 of the sleeve 11 has a straight section. The external sleeve 11 is hollow, and a cannula 13 extends along a longitudinal axis A into an internal volume 14 of said external sleeve 11. The cannula 13, also hollow, has a generally cylindrical shape with a straight circular cross-section, concentric with the external sleeve 11. The inner diameter d of the cannula 13 is strictly less than the inner diameter D of the external sleeve 11, so that a movement along the axis A of the cannula 13 with respect to the external sleeve 11, or conversely, is possible without friction.

The cannula 13 includes a tapered distal point 15. In the example shown in FIGS. 1 and 2, the distal point 15 of the cannula 13 extends in protrusion from the right distal end 12 of the external sleeve 11. Thus, when the system 10 must pass through a target osseous body, it is the tapered distal point 15 of the cannula 13 which enters first into contact with the body, facilitating penetration. In another exemplary embodiment, as shown in FIG. 3, the distal end 12 of the sleeve 11, with a constant diameter, is beveled, and the distal point 15 of the cannula 13 is flush with the orifice of the distal end 12. In this case, it is the beveled end of the sleeve 11 and the distal point 15 of the cannula 13 which enter simultaneously into contact with the osseous body, the beveled shape of the sleeve 11 also aiding penetration.

An opening 17 is provided, in a distal portion 16 of the cannula 13. The opening 17 must have sufficient dimensions to allow the passage of cement flowing through the cannula 13. A stent 18 is wound around the distal portion 16 of the cannula 13. The stent 18 is positioned on the cannula 13 so as to be entirely accommodated in the internal volume 14 of the external sleeve 11, and held in space between the cannula and the sleeve. The stent is advantageously a self-expanding stent with shape memory. The stent 18 is held in a constrained state, i.e. not deployed, in the internal volume 14 of the sleeve 11.

FIGS. 4A and 4B show two examples of a stent 18 which can be used in the system 10 for intraosseous injection of cement according to the invention. Advantageously, the meshing of the stent 18 is such that leakage of cement out of said stent is limited. According to one particular embodiment, as shown in FIG. 4B, the stent 18 is entirely covered by a film 19.

The film 19 allows the risks of leakage to be further reduced. For example, the film 19 is made of a sealed elastic material, and for example of PTFE.

Blocking means (not shown) advantageously allow the cannula 13 to be held reversibly in this first position, or penetration position, in the external sleeve 11. For example, the proximal ends of the external sleeve 11 and of the cannula 13 are provided with complementary threads, prohibiting any sliding of the cannula 13 in the external sleeve 11. Movement of the cannula 13 with respect to the external sleeve 11, and conversely, is then only possible by turning one with respect to the other, in the direction allowed by the screw pitch.

FIG. 2 shows the system 10 in use. More precisely, the external sleeve 11 has been pulled back toward the proximal end of the cannula 13, opposite to the distal end 15. This longitudinal movement by a distance L allows the distal portion 16 of the cannula and the stent to be released. The stent 18 no longer being held between the internal walls of the external sleeve 11 and the cannula 13, it can deploy to resume its initial shape.

The cannula 13 and/or the sleeve 11 can be provided with visual references (not shown) allowing the user to be informed of the movement, sufficient or not, of the sleeve with respect to the cannula, and therefore of the complete releasing of the stent 18. The visual means are advantageously situated at the proximal parts of the cannula 13 and/or of the sleeve 11 so as to be outside the body of the patient during the use of the system 10.

Advantageously, in this second position, the opening 17 of the cannula 13 is located entirely in the internal volume of the stent 18. If necessary, it is practicable to move the cannula 13 along the axis A, so as to position the opening 17 at the desire location with respect to the stent 18, and allow, during the injection of the cement, a uniform distribution of the cement in the entire volume of the stent 18.

A method of intraosseous injection of surgical cement will now be described using FIGS. 5A-5G. Such a method is advantageously implemented during the treatment of a patient, particularly a human, having bone trauma. For example, such a method can be implemented to accomplish a stentoplasty at a damaged vertebra.

Figure 5A:
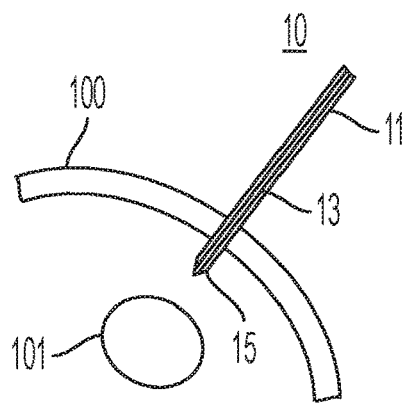
Figure 5B:
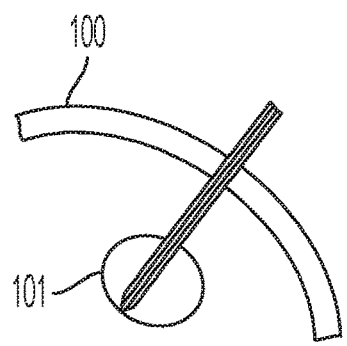

As can be seen in FIG. 5A, the system 10 for injecting surgical cement according to the invention is brought into the body 100 of a patient by the tapered distal end 15 of the cannula 13, which first pierces and passes through the body 100 of the patient. The cannula 13/external sleeve 11 assembly is inserted into the body 100 of the patient up to the target osseous body 101 (FIG. 5B).

Figure 5C:
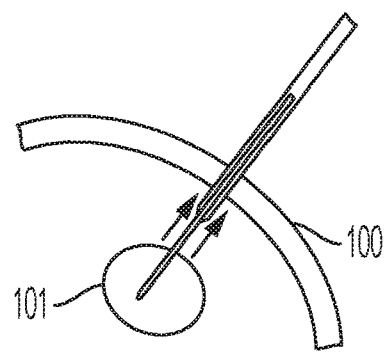
Figure 5D:
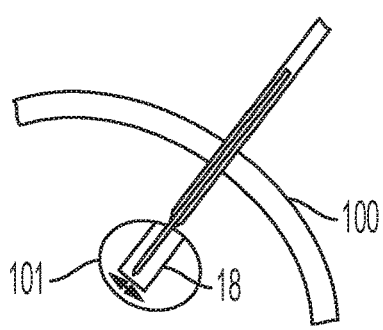

The external sleeve 11 is then withdrawn at least partially from the body 100 of the patient. Only the cannula 13, on which the stent 18 is mounted, remains in position in the osseous body 101 (FIG. 5C). The stent 18 can then deploy in the osseous body 101 (FIG. 5D).

Figure 5E:
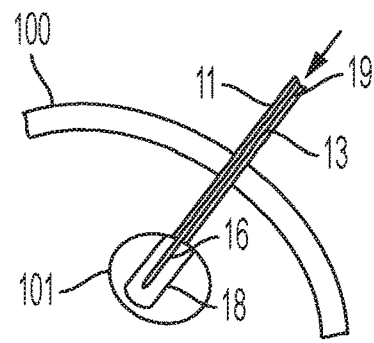
Figure 5F:
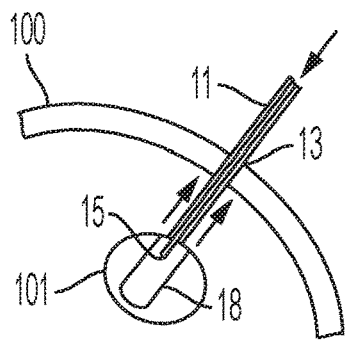
Figure 5G:
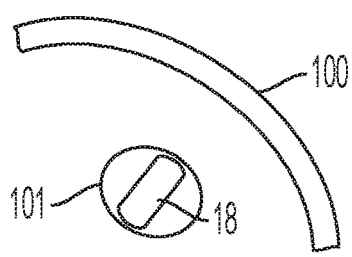

Cement injection means (not shown), coupled to the proximal end 19 of the cannula 13, allow cement to be injected through the cannula 13 into the stent 18 (FIG. 5E). For example, a syringe filled with surgical cement is inserted into the cannula 13 by its proximal end. The piston of the syringe is then inserted into said syringe to cause the cement to penetrate into the cannula. The cement flows out of the cannula 13 by the lateral opening (not visible) and fills the internal volume of the stent 18. During the cement injection phase, the cannula 13 is withdrawn progressively from the osseous body 101 (FIG. 5F), the external sleeve 11, for its part, being able to be held in position. It is also possible to begin to progressively withdraw the cannula/sleeve assembly.

When the entire internal volume of the stent 18 is filled with cement, the cannula 13 and the external sleeve 11 are completely withdrawn from the body 100 of the patient, leaving only the stent 18 containing the cement in position in the osseous body 101.

The invention claimed is:

1. A system for intraosseous injection of surgical cement consisting of:
    an external sleeve having an inner wall and an outer wall;
    a cannula mounted coaxially within the external sleeve and having an interior and exterior, said cannula being able to be moved along a longitudinal axis in the external sleeve, the cannula including a closed integrated tapered distal point that facilitates the insertion of the system into the osseous body and a lateral opening allowing cement to pass from the interior to the exterior of said cannula, and the cannula being connectable to a cement injector; and
    a stent accommodated in the interior of the external sleeve, said stent being mounted around an external wall of a distal portion of the cannula.

2. The system for the intraosseous injection of surgical cement according to claim 1, wherein the tapered distal point leads to the outside of the external sleeve.

3. The system for the intraosseous injection of surgical cement according to claim 1, wherein the external sleeve is provided with a beveled distal point.

4. The system for the intraosseous injection of surgical cement according to claim 1, wherein the stent is self-expanding.

5. The system for the intraosseous injection of surgical cement according to claim 4, wherein the stent is made of shape-memory material.

6. The system for the intraosseous injection of surgical cement according to claim 1, wherein the stent is entirely covered with an anti-leakage film.

7. The system for the intraosseous injection of surgical cement according to claim 6, wherein the anti-leakage film is made of polytetrafluoroethylene (PTFE).

8. The system for the intraosseous injection of surgical cement according to claim 1, wherein the external sleeve and the cannula have a straight profile.

9. The system for the intraosseous injection of surgical cement according to claim 1, wherein at least a distal end of the external sleeve and of the cannula have a curved profile.

10. An intraosseous surgical cement injection kit comprising a system as set forth in claim 1 and a cement injector capable of being connected to a proximal end of the cannula.

11. The intraosseous surgical cement injection kit according to claim 10 further comprising surgical cement.

12. The intraosseous surgical cement injection kit according to claim 10, further comprising an anti-leakage film surrounding the stent.

13. The intraosseous surgical cement injection kit according to claim 12, wherein the anti-leakage film is made of polytetrafluoroethylene (PTFE).

14. The system for the intraosseous injection of surgical cement according to claim 1, wherein the stent is constrained between the external wall of the cannula and the internal wall of the sleeve.

15. The system for the intraosseous injection of surgical cement according to claim 1, wherein the external sleeve and the cannula are provided with complementary threads that prohibit sliding of the cannula in the external sleeve.

\* \* \* \* \*